US006897201B2

(12) United States Patent
Boyer et al.

(10) Patent No.: US 6,897,201 B2
(45) Date of Patent: May 24, 2005

(54) COMPOSITIONS AND METHODS FOR THE TREATMENT OF GLAUCOMA OR OCULAR HYPERTENSION

(75) Inventors: Jose L. Boyer, Chapel Hill, NC (US); Benjamin R. Yerxa, Raleigh, NC (US); Robert Plourde, Jr., Chapel Hill, NC (US); Edward G. Brown, Cary, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 10/087,551

(22) Filed: Feb. 27, 2002

(65) Prior Publication Data

US 2002/0128224 A1 Sep. 12, 2002

Related U.S. Application Data

(63) Continuation-in-part of application No. 09/934,970, filed on Aug. 21, 2001, which is a continuation-in-part of application No. 09/643,138, filed on Aug. 21, 2000.

(51) Int. Cl.[7] .......................... A61K 31/70; A01N 43/04
(52) U.S. Cl. ............................. 514/51; 514/47; 514/48; 514/49; 514/50; 514/52; 514/81; 536/26.23; 536/26.26; 544/264; 544/265
(58) Field of Search ............................. 514/47, 48, 49, 514/50, 51, 52, 81; 536/26.23, 26.26; 544/264, 265

(56) References Cited

U.S. PATENT DOCUMENTS

| 5,219,849 A | 6/1993 | Lotti et al. .................... 514/214 |
| 5,545,626 A | 8/1996 | Stein et al. .................... 514/44 |
| 5,654,285 A | 8/1997 | Ingall et al. .................... 514/47 |
| 5,721,219 A | 2/1998 | Ingall et al. .................... 514/47 |
| 5,747,496 A | 5/1998 | Cox et al. .................... 514/258 |
| 5,955,447 A | 9/1999 | Ingall et al. .................... 514/47 |
| 6,166,022 A | 12/2000 | Brown et al. ................ 514/258 |
| 6,323,187 B1 * | 11/2001 | Yerxa et al. .................... 514/51 |

FOREIGN PATENT DOCUMENTS

| WO | WO 92/17488 | 10/1992 |
| WO | WO 94/18216 | 8/1994 |
| WO | WO 97/03084 | 1/1997 |
| WO | WO 98/28300 | 7/1998 |
| WO | WO 00/03741 | 1/2000 |
| WO | WO 00/33080 | 6/2000 |
| WO | WO 00/34283 | 6/2000 |
| WO | WO 01/19826 | 3/2001 |
| WO | WO 01/36421 | 5/2001 |
| WO | WO 01/39781 | 6/2001 |
| WO | PCT/US03/06685 | 2/2003 |

OTHER PUBLICATIONS

Chambers, et al., "A G Protein–coupled Receptor for UDP–glucose," *J. Biol. Chem.*, 275:10767–10771 (2000).
Crawford, et al., "Agonist–induced $Ca^{2+}$ mobilization in cultured bovine and human corneal endothelial cells," *Current Eye Res.*, 12(4): 303–311 (1993).
Jumblatt and Jumblatt, "Regulation of Ocular Mucin Secretion by $P2Y_2$ Nucleotide Receptors in Rabbit and Human Conjunctive," *Exp. Eye Res.*, 67(3):341–6 (1998).
Peral, et al., "Effects of diadenosine polyphosphates on intraocular pressure and pupil size in New Zealand rabbits," *Investig. Opthalmol. Vis. Science*, 41:S255 (2000).
Pintor, et al., "Effect of ATP and adenine nucleotides on Intraocular pressure in New Zealand rabbits," *Investig. Opthalmol. Vis. Science*, 41:S255 (2000).
Roetth, "Lenticular Opacities in Glaucoma Patients Recieving Echothiophate Iodide Therapy," *J.A.M.A.*, 195:644–666 (1966).
Simon, et al., "Convenient Syntheses of Cytidine 5'–Triphosphate, Guanosine 5'–Triphosphate, and Uridine 5'–Triphosphate and Their Use in the Preparation of UDP–glucose, UDP–gluconic Acid, and GDP–mannose," *J. Org. Chem.*, 55:1834–1841 (1990).
Wax and Coca–Prados, "Receptor–Mediated Phosphoinositride Hydrolysis in Human Ocular Ciliary Epithelial Cells," *Ivestig. Opthalmol. Vis. Science*, 30(7):1675–1679 (1989).
Wax, et al., "Purinergic Receptors in Ocular Ciliary Epithelial Cells," *Exp. Eye Res.*, 57: 89–95 (1993).

* cited by examiner

*Primary Examiner*—Samuel Barts
*Assistant Examiner*—Patrick Lewis
(74) *Attorney, Agent, or Firm*—Howrey Simon Arnold and White; Viola T. Kung

(57) ABSTRACT

The present invention is directed to a method of reducing intraocular pressure. The method comprises administering to a subject a pharmaceutical composition comprising an effective amount of a nucleoside 5'-pyrophosphate pyranoside or analogue, which is defined by general Formula I. The method of the present invention is useful in the treatment or prevention of ocular hypertension, such as found in glaucoma, including primary and secondary glaucoma. The method can be used alone to reduce intraocular pressure. The method can also be used in conjunction with another therapeutic agent or adjunctive therapy commonly used to treat glaucoma to enhance the therapeutic effect of reducing the intraocular pressure. The present invention also provides a novel composition comprising a nucleoside 5'-pyrophosphate pyranoside or analogues.

11 Claims, 1 Drawing Sheet

COMPOSITIONS AND METHODS FOR THE TREATMENT OF GLAUCOMA OR OCULAR HYPERTENSION

This application is a continuation-in-part of U.S. application Ser. No. 09/934,970, filed Aug. 21, 2001; which is a continuation-in-part of U.S. application Ser. No. 09/643,138, filed Aug. 21, 2000.

TECHNICAL FIELD

This invention relates to a method of lowering intraocular pressure and thereby treating ocular hypertension and/or glaucoma.

BACKGROUND OF THE INVENTION

Glaucoma is a slowly progressive blinding disease usually associated with chronic elevation of intraocular pressure (IOP). Sufficiently high and persistent intraocular pressure is believed to result in damage to the optic disc at the juncture of the optic nerve and retina, resulting in degeneration of retinal ganglion cells and blindness characteristic of glaucoma. However, the mechanism whereby IOP elevation (also known as ocular hypertension) leads to glaucoma is not well understood. Additionally, a fraction of patients with typical visual field loss associated with glaucoma do not show abnormal elevated IOP levels (known as low-tension or normal-tension glaucoma).

Glaucoma is primarily classified as open-angle, closed-angle, or congenital, and further classified as primary and secondary. Glaucoma is treated with a variety of pharmacological and surgical approaches. In cases where glaucoma is associated with ocular hypertension, pharmacological treatment comprises adrenergic agonists (epinephrine, dipevefrin, apraclonidine), cholinergic agonists (pilocarpine), beta blockers (betaxolol, levobunolol, timolol), carbonic anhydrase inhibitors (acetazolamide) or more recently, prostaglandin analogues (latanoprost, Lumigan™) and alpha adrenergic agonists (brimonidine). These pharmacological approaches help restore the IOP to a normotensive state either by inhibiting the production of aqueous humor by the ciliary body, or facilitating aqueous humor outflow across the trabecular meshwork. The congenital form of glaucoma rarely responds to therapy and is more commonly treated with surgery. In narrow angle glaucoma, the aqueous outflow is enhanced by freeing of the entrance to the trabecular space at the canal of Schlemm from blockade by the iris, as a result of the drug-induced contraction of the sphincter muscle of the iris (Taylor, pp. 123–125, in *The Pharmacological Basis of Therapeutics, 7$^{th}$ Ed*, Eds., A. G. Gilman, L. S. Goodman, T. W. Rall, and F. Murad, MacMillan Publishing Company, New York, (1985)).

In wide-angle, or chronic simple, glaucoma, the entry to the trabeculae is not physically obstructed; the trabeculae, a meshwork of pores of small diameter, lose their patency. Contraction of the sphincter muscle of the iris and the ciliary muscle enhances tone and alignment of the trabecular network to improve resorption and outflow of aqueous humor through the network to the canal of Schlemm (Watson, *Br. J. Opthalmol.*, 56: 145–318 (1972); Schwartz, *N. Engl. J. Med.*, 290: 182–186 (1978); Kaufman, et al., *Handbook of Experimental Pharmacology*, 69: 149–192 (1984)).

Acute congestive (narrow angle) glaucoma is nearly always a medical emergency in which the drugs are essential in controlling the acute attacks, but long-range management is usually based predominantly on surgery (peripheral or complete iridectomy). By contrast, chronic simple (wide-angle) glaucoma has a gradual, insidious onset and is not generally amenable to surgical improvement; and control of intraocular pressure depends upon permanent therapy.

Acute congestive glaucoma may be precipitated by the injudicious use of a mydriatic agent in patients over 40 years, or by a variety of factors that can cause pupillary dilatation or engorgement of intraocular vessels. Signs and symptoms include marked ocular inflammation, a semidilated pupil, severe pain, and nausea. The therapeutic objective is to reduce the intraocular pressure to the normal level for the duration of the attack. An anticholinesterase agent is instilled into the conjunctival sac with a parasympathomimetic agent for greatest effectiveness. A commonly used combination consists of a solution of physostigmine and salicylate, 0.5%, plus pilocarpine nitrate, 4%. Adjunctive therapy includes the intravenous administration of a carbonic anhydrase inhibitor such as acetozolamide to reduce the secretion of aqueous humor, or of an osmotic agent such as mannitol or glycerin to induce intraocular dehydration.

Therapy of chronic simple glaucoma and secondary glaucoma includes: (1) prostaglandin analogs (e.g. Xalatan®, Lumigan); (2) beta-adrenergic antagonists such as timolol maleate; (3) sympathomimetic agents (e.g. epinephrine, brimonidine); (4) cholinergic agents (e.g. pilocarpine nitrate, echothiophate iodide; and (5) carbonic anhydrase inhibitors (e.g. Dorzolamide®) (Dain Rauscher Wessels, *Glaucoma in the 21$^{st}$ Century: New Ideas, Novel Treatments* (2001)).

Latanaprost (Xalatan®) is a prostanoid agonist that is believed to reduce IOP by increasing the uveoscleral outflow of aqueous humor. Latanoprost is an isopropyl ester prodrug, and is hydrolyzed by esterases in the cornea to the biologically active acid. Xalatan® (0.005%) is prescribed for once-daily dosing and is shown to be equivalently effective as twice-daily dosing of 0.5% timolol. However, Xalatan® may gradually change eye color by increasing the amount of brown pigment in the iris. The long-tern effect on the iris is unknown. Eyelid skin darkening has also been reported in associated with the use of Xalatan®. In addition, Xalatan® may gradually increase the length, thickness, pigmentation, and number of eyelashes. Macular edema, including cystoid macular edema, has been reported during treatment with Xalatan®. These reports have mainly occurred in aphakic patients, in pseudophakic patients with a torn posterior lens capsule, or in patients with known risk factors for macular edema (Ophthalmic PDR, 315–316 (2001)).

Beta-Adrenergic antagonists effectively lower IOP when administered twice daily as a topical solution. The mechanism of reduction is through inhibition of the production of aqueous humor formed by the ciliary body. Topical timolol causes fewer adverse effects than the anticholinesterase agents. However, it may induce hyperaemia of the conjunctiva, burning, stinging, and superficial punctate keratitis (Van Buskirk, *Ophthalmology*, 87: 447–450 (1980)). It may also reduce tear flow, causing dry eye syndrome (Coakes, et. al., *Br. J. Ophthalmol*, 65: 603–605 (1981)). A more serious side effect of beta-blockers is cardiac failure, thus this class of IOP-lowering agent is not indicated with cardiopulmonary disease.

Alpha-Adrenergic agonists, such as brimonidine and apraclonidine, control IOP by reducing the production of aqueous humor as well as enhancing uveoscleral outflow (Burke & Schwartz, *Survey of Ophthalmology*, 41:S9–S18 (1996)). Topical ophthalmic solutions are absorbed systemically and can produce dry mouth, ocular hyperemia, headache, and foreign body sensation (Hoyng and van Beek, *Drugs*, 59: 411–434 (2000)).

The use of long-acting anticholinesterase agents is associated with a greater risk of developing lenticular opacities and untoward autonomic effects. Treatment of glaucoma with potent, long-acting anticholinesterase agents (including demecarium, echothiophate, and isoflurophate) for 6 months or longer is associated with a high risk of developing cataracts (Axelsson, et al., *Acta Opthalmol. (Kbh.)*, 44:

421–429 (1966); de Roetth, *J.A.M.A.*, 195: 664–666 (1966); Shaffer, et al., *Am. J. Opthalmol.*, 62: 613–618 (1966)). Although development of cataracts is common in untreated comparable age groups, the incidence of lenticular opacities under such circumstances can reach 50%, with the risk increasing in proportion to the strength of the solution, frequency of instillation, duration of therapy, and age of patient (Laties, *Am. J. Opthalmol.*, 68: 848–857 (1969); Kaufman, et al., pp. 149–192, in *Pharmacology of the Eye, Handbook of Experimental Pharmacology*, Vol. 69, Ed. M. L. Sears, Springer-Verlag, Berlin, (1984)).

Miscellaneous ocular side effects that may occur following instillation of anticholinesterase agents are headache, brow pain, blurred vision, phacodinesis, pericorneal injection, congestive iritis, various allergic reactions and, rarely, retinal detachment. When anticholinesterase drugs are instilled intraconjunctivally at frequent intervals, sufficient absorption may occur to produce various systemic effects that result from inhibition of anticholinesterase and butyryl-cholinesterase. Hence, cholinergic autonomic function may be enhanced, the duration of action of local anesthetics with an ester linkage prolonged, and succinylcholine-induced neuromuscular blockade enhanced and prolonged. Individuals with vagotonia and allergies are at particular risk.

Because the cholinergic agonists and cholinesterase inhibitors block accommodation, they induce transient blurring of far vision, usually after administration of relatively high doses over shorter duration. With long-term administration of the cholinergic agonists and anticholinesterase agents, the response diminishes due to a diminished number of acetylcholine receptors.

Long-acting anticholinesterase agents are not recommended when prostaglandin analogs, beta-adrenergic antagonists, sympathomimetic agonists, or other agents can control glaucoma.

Carbonic anhydrase inhibitors control IOP by inhibiting the formation of aqueous humor. Oral carbonic anhydrase inhibitors exhibit pronounced systemic side effects, but newer topical solutions have a better side effect profile. Frequent side effects associated with topical Dorzolamide® include burning and stinging, bitter taste, superficial punctate keratitis, and allergic reaction (Hoyng and van Beek, *Drugs*, 59: 411–434 (2000)).

Other new agents have been assessed for treatment of glaucoma, including an $A_3$ subtype adenosine receptor antagonist, a calmodulin antagonist, and an antiestrogen (WO 00/03741); an oligonucleotide which may be substituted, or modified in its phosphate, sugar, or base so as to decrease intraocular pressure (U.S. Pat. No. 5,545,626); and a class of pyrazine, pyrimidine, and pyridazine derivatives, substituted by a non-aromatic azabicyclic ring system and optionally by up to two further substituents (U.S. Pat. No. 5,219,849).

Various studies have documented the presence of purinergic receptors in the eye. Activation of $P2Y_2$ receptors in rabbit and human conjunctival cells was associated with an increase in mucin secretion (Jumblatt and Jumblatt, *Exp. Eye Res.*, 67(3):341–6 (1998)). $P2Y_2$ receptor agonists, such as ATP, cause mucin secretion, and mechanical stimulus of the cornea triggers local ATP release (Jensen et al., poster presentation at American Academy of Optometry annual meeting, December, 1999, Seattle, Wash.). Studies of purinergic receptors in ocular ciliary epithelial cells demonstrated a $P2_U$ purinergic receptor, that was preferentially coupled to UTP and associated with the stimulation of phosphoinositide hydrolysis in both bovine pigmented and human non-pigmented epithelial cells (Wax, et al, *Exp. Eye Res.*, 57: 89–95 (1993)). ATP significantly increased formation of inositol phosphates in bovine corneal endothelial cells (Crawford, et al., *Current Eye Res.*, 12(4): 303–311 (1993) and in human ocular ciliary epithelial cells (Wax and Coca-Prados, *Investig. Opthalmol. Vis. Science*, 30 (7): 1675–1679 (1989)). Diadenosine tetraphosphate has been shown to lower intraocular pressure in rabbits (Peral, et.al, *Investig. Opthalmol. Vis. Science*, 41: S255 (2000). Alpha, Beta-Methylene adenosine triphosphate and beta, gamma methylene adenosine triphosphate also were shown to reduce intraocular pressure in rabbits (Pintor, et.al., *Investig. Opthalmol. Vis. Science*, 41: S255 (2000). Recently a new G-protein coupled receptor (GPCR) that is selective for nucleotide pyranose esters such as uridine 5'-diphospho-α-D-glucose (UDPG), UDP-galactose, UDP-glucuronic acid and UDP-N-acetylglucosamine were described (J. K. Chambers, et al., *J. Biol. Chem.*, Vol. 275, p. 10767–10771 (2000)). This receptor shares a fairly high degree of homology with the P2Y family of receptors and is expressed widely in the central nervous system (CNS) as well as in peripheral tissues. Although characterization of the receptor showed that it responded to a discreet set of naturally occurring nucleotide pyranose esters, the physiological role of such activation has yet to be determined.

As described above, agents commonly used to treat glaucoma may cause adverse side effects, such as eye pain, eye color darkening, headache, blurred vision or the development of cataracts. There exists a need for agents that are both safe and effective in the treatment of glaucoma.

SUMMARY OF THE INVENTION

The present invention is directed to a method of reducing intraocular pressure. The method comprises administering to a subject a pharmaceutical composition comprising an effective amount of a nucleoside 5'-pyrophosphate pyranoside of general Formula I. Optionally, the method comprises an additional step of measuring the intraocular pressure of the subject before and/or after administering the composition. The methods of the present invention are useful in the treatment or prevention of conditions associated with elevated intraocular pressure such as ocular hypertension or glaucoma.

The nucleoside 5'-pyrophosphate pyranosides and analogues useful for this invention are compounds of general Formula I, or pharmaceutically acceptable salts thereof:

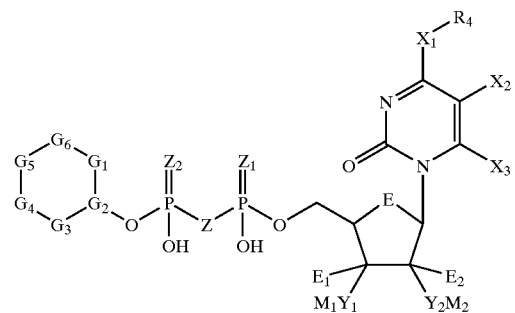

Formula I

The present method can be used alone to reduce intraocular pressure. The method can also be used in conjunction with other therapeutic agents or adjunctive therapies commonly used to treat ocular hypertension or glaucoma to enhance the therapeutic effect of reducing the intraocular pressure.

DETAILED DESCRIPTION OF THE INVENTION

Figure 1:
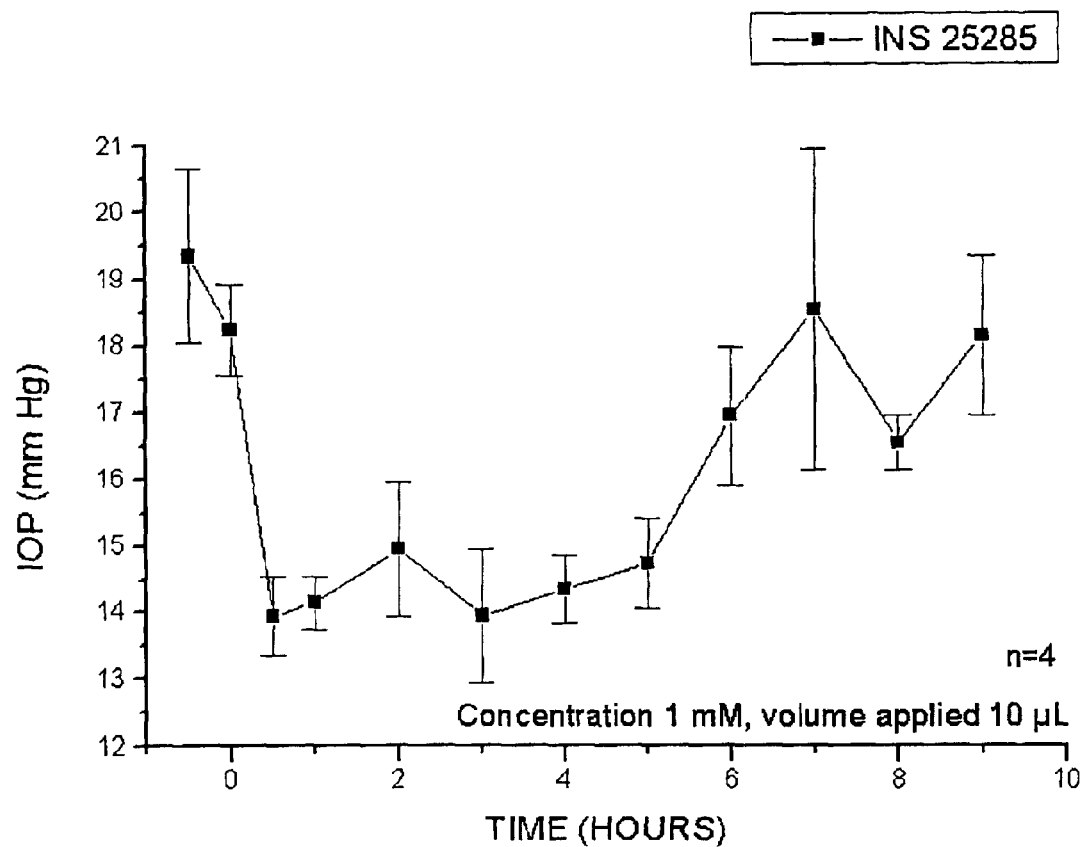
FIG. 1 shows the reduction of intraocular pressure in New Zealand white rabbits by uridine 5'-diphospho-α-D-glucopyranoside.

The present invention provides a method of reducing intraocular pressure in a subject, thus treating disorders associated with elevated intraocular pressure. The method comprises administering to a subject a pharmaceutical composition comprising an effective amount of a nucleoside 5'-pyrophosphate pyranoside or analogue. Optionally, the method comprises an additional step of measuring the intraocular pressure of the subject before and/or after administering the composition. The methods of the present invention are useful in the treatment or prevention of conditions associated with elevated intraocular pressure such as ocular hypertension or glaucoma. An effective amount of a nucleoside 5'-pyrophosphate pyranoside or analogue is an amount that reacts with a nucleoside 5'-pyrophosphate pyranoside receptor (a G-protein coupled receptor, correct), leading to a reduction in intraocular pressure and/or amelioration of the symptoms of glaucoma.

The method of the present invention is useful for the management and/or treatment of primary glaucoma, which consists of two types: narrow angle or acute congestive and wide angle or chronic simple glaucoma. The method of the present invention is also useful for the management and/or treatment of secondary glaucoma.

Description of Compounds

The nucleoside 5'-pyrophosphate pyranosides and analogues useful for the present method include all compounds, diastereomers, enantiomers and tautomers of Formula I, or salts thereof:

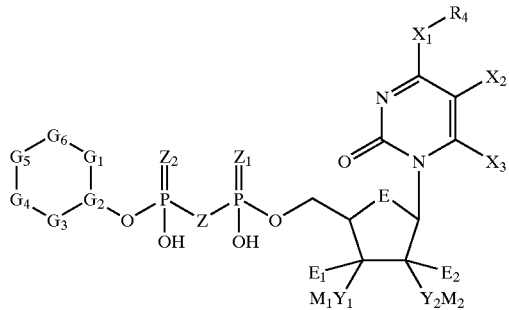

Formula I wherein:

$X_1$=O, NR, S, $CF_2$, $CF_3$ or CN with the proviso that when $X_1$=$CF_3$ or CN, then $R_4$ is absent; or $X_1$ represents a bond from the pyrimidine ring to $R_4$;

$X_2$=H, F, Cl, Br, I, CN, $OR_8$, $SR_8$, $NR_9R_{13}$, $CF_3$, alkyl, cycloalkyl, arylalkyl, aryl, arylalkenyl, arylalkynyl, $C(O)R_{16}$, $C(O)OR_{17}$, $C(O)NR_{16}R_{18}$ or heterocycle of 5 to 7 members;

$X_3$=H, CN, $OR_{19}$, $SR_{19}$, $NR_{23}R_{28}$, $CF_3$, alkyl, cycloalkyl, $C(O)R_{32}$, $C(O)OR_{33}$, $C(O)NR_{34}R_{35}$, arylalkyl, aryl, arylalkenyl, arylalkynyl, or a heterocycle of 5 to 7 members;

R=H, $OR_1$, alkyl, cycloalkyl, arylalkyl, aryl, $C(O)R_2$, $C(O)OR_3$ or $C(O)NR_1R_2$;

$R_1$, $R_7$, $R_{10}$, $R_{22}$, $R_{24}$, $R_{27}$, $R_{31}$, $R_{33}$ and $R_{35}$ are each independently H, alkyl, cycloalkyl, arylalkyl or aryl;

$R_2$=H, alkyl, cycloalkyl, arylalkyl, aryl or heterocyclic ring of 5 to 7 members; or $R_1$ and $R_2$ taken together can form a heterocyclic ring of 5 to 7 members;

$R_3$, $R_6$, $R_8$, $R_{12}$, $R_{15}$, $R_{17}$, $R_{21}$, $R_{26}$ and $R_{30}$ are independently alkyl, cycloalkyl, arylalkyl, or aryl;

$R_4$=H, alkyl, cycloalkyl, arylalkyl, aryl, heterocyclic ring of 5 to 7 members, $C(O)R_5$, $C(O)OR_6$ or $C(O)NR_5R_7$;

$R_5$, $R_{11}$, $R_{14}$, $R_{16}$, $R_{18}$, $R_{20}$, $R_{25}$, $R_{29}$, $R_{32}$ and $R_{34}$ are independently H, alkyl, cycloalkyl, arylalkyl, aryl or heterocyclic ring of 5 to 7 members;

$R_9$=H, $OR_{10}$, alkyl, cycloalkyl, arylalkyl, aryl, $C(O)R_{11}$, $C(O)OR_{12}$ or $C(O)NR_{10}R_{11}$;

$R_{13}$=H, alkyl, cycloalkyl, arylalkyl, aryl, $C(O)R_{14}$ or $C(O)OR_{15}$;

$R_{19}$=alkyl, cycloalkyl, arylalkyl, or aryl, $C(O)R_{20}$, $C(O)OR_{21}$ or $C(O)NR_{20}R_{22}$;

$R_{23}$=H, $OR_{24}$, alkyl, cycloalkyl, arylalkyl, aryl, $C(O)R_{25}$, $C(O)OR_{26}$ or $C(O)NR_{25}R_{27}$;

$R_{28}$=H, alkyl, cycloalkyl, arylalkyl, aryl, $C(O)R_{29}$, $C(O)OR_{30}$ or $C(O)NR_{29}R_{31}$;

where $R_{26}$ and $R_{29}$ taken together can form a heterocyclic ring of 6 or 7 members;

or $R_2$ and $R_4$, $R_2$ and $R_5$, $R_{10}$ and $R_{11}$, $R_9$ and $R_{13}$, $R_{10}$ and $R_{13}$, $R_9$ and $R_{14}$, $R_{11}$ and $R_{14}$, $R_9$ and $R_{15}$, $R_{11}$ and $R_{15}$, $R_{16}$ and $R_{18}$, $R_{20}$ and $R_{22}$, $R_{25}$ and $R_{27}$, $R_{23}$ and $R_{28}$, $R_{24}$ and $R_{28}$, $R_{25}$ and $R_{28}$, $R_{25}$ and $R_{29}$, $R_{29}$ and $R_{31}$ or $R_{34}$ and $R_{35}$ are optionally taken together to form a heterocyclic ring of 5 to 7 members;

E=O or $CH_2$;

$E_1$ and $E_2$ independently are H or F; or $E_1$ and $E_2$, when taken together, form a carbon-carbon bond;

$Y_1$=O or F, with the proviso that when $Y_1$=F, then $M_1$ is absent; or $Y_1$ represents a bond from the point of ring attachment to $M_1$;

$Y_2$=O or F, with the proviso that when $Y_2$=F, then $M_2$ is absent; or $Y_2$ represents a bond from the point of ring attachment to $M_2$;

$M_1$ and $M_2$ are independently H, alkyl, cycloalkyl, arylalkyl, aryl, $C(O)M_3$, $C(O)OM_4$, or $C(O)NM_3M_5$;

$M_3$=H, alkyl, cycloalkyl, arylalkyl, aryl or heterocyclic ring of 5 to 7 members;

$M_4$=alkyl, cycloalkyl, arylalkyl or aryl;

$M_5$=H, alkyl, cycloalkyl, arylalkyl, or aryl; or $M_3$ and $M_5$ taken together form a heterocyclic ring of 5 to 7 members;

when $Y_1$=$Y_2$=O, $M_1$ and $M_2$ optionally are bonds from the oxygen atoms of $Y_1$ and $Y_2$, respectively, to a carbon atom of an acetal-, ketal- or orthoester group $E_3$;

wherein $E_3$ is $Q(A_1)(A_2)$;

wherein Q is a carbon atom;

$A_1$=H, $CF_3$, alkyl, cycloalkyl, arylalkyl or aryl;

$A_2$=H, $OA_3$, $CF_3$, alkyl, cycloalkyl, arylalkyl, aryl or heterocycle of 5 to 7 members;

$A_3$=alkyl, cycloalkyl, arylalkyl or aryl; or where $A_1$ and $A_2$, when taken together, form a carbocyclic ring of 5 or 6 members, with or without unsaturation, and with or without substitution; or $M_1Q(A_1)(A_2)M_2$ is taken together to form a carbonyl bonded to $Y_1$ and $Y_2$, such that a cyclic carbonate is formed;

Z=O, $NZ_3$, $CH_2$, CHF, $CF_2$, $CCl_2$, or CHCl;

$Z_1$ and $Z_2$ are independently O or S;

$Z_3$=H, alkyl, cycloalkyl, arylalkyl, aryl or a heterocyclic ring of 5 to 7 members;

$G_1$=O, S, $CH_2$ or $CH(OJ_1)$;

$G_2$=CH, $C(CH_2OJ_3)$, $CCH_3$, $CCF_3$, or $C(CO_2J_4)$;

$G_3$=$CH_2$, CHF, $CF_2$, $CH(OJ_5)$ or $CH(NJ_6J_7)$;

$G_4$=$CH_2$, CHF, $CF_2$, $CH(OJ_9)$, or $CH(NJ_{11}J_3)$;

$G_5$=$CH_2$, CHF, $CF_2$, $CH(OJ_{15})$, or $CH(NJ_{16}J_{17})$;

$G_6$=$CH_2$, $CH(CH_3)$, $CH(CHF_2)$, $CH(CF_3)$, $CH(OJ_{19})$, $CH(CH_2OJ_{19})$, $CH(CH_2(NJ_{21}J_{23}))$, or $CH(CO_2J_{22})$, with the provision that when $G_1$=O or S, then $G_6$ does not equal CH(OH); and the number of hydrogen atoms bonded to the $G_1$–$G_6$ ring atoms is limited to a maximum of 8;

also with the provision that the number of nitrogen atoms bonded to the $G_1$–$G_6$ ring atoms in Formula I is limited to a maximum of 2;

$J_1$=H, alkyl, cycloalkyl, arylalkyl, aryl, or $C(O)J_2$;

$J_2$, $J_6$, $J_8$, $J_{10}$, $J_{11}$, $J_{14}$, $J_{16}$, $J_{18}$, $J_{20}$, $J_{22}$, and $J_{24}$ are independently H, alkyl, cycloalkyl, arylakyl, aryl or heterocyclic ring of 5 to 7 members;

$J_3$=alkyl, cycloalkyl, arylalkyl, aryl or $C(O)J_2$;

$J_4$=alkyl, cycloalkyl, arylalkyl, aryl or heterocyclic ring of 5 to 7 members;

$J_5$=H, alkyl, cycloalkyl, arylalkyl, aryl, or $C(O)J_6$;

$J_7$=H, alkyl, cycloalkyl, arylalkyl, aryl or $C(O)J_8$;

$J_9$=H, alkyl, cycloalkyl, arylalkyl, aryl, $C(O)J_{10}$, $CH(CH_3)(CO_2J_{11})$, or $CH(CH_3)(C(O)NJ_{11}J_{12})$;

$J_{12}$=H, alkyl, cycloalkyl, arylalkyl, aryl, heterocyclic ring of 5 to 7 members, an amino acid radical of 2 to 12 carbon atoms with or without hetero atoms, or a peptide radical comprising 2 to 10 amino acid units;

$J_{13}$=H, alkyl, cycloalkyl, arylalkyl, aryl or $C(O)J_{14}$;

$J_{15}$=H, alkyl, cycloalkyl, arylalkyl, aryl or $C(O)J_{16}$;

$J_{17}$=H, alkyl, cycloalkyl, arylalkyl, aryl or $C(O)J_{18}$;

$J_{19}$=H, alkyl, cycloalkyl, arylalkyl, aryl or $C(O)J_{20}$;

$J_{21}$=H, alkyl, cycloalkyl, arylalkyl, aryl, $C(O)J_{22}$ or heterocyclic ring of 5 to 7 members;

$J_{23}$=H, alkyl, cycloalkyl, arylalkyl, aryl or $C(O)J_{24}$; or $J_6$ and $J_7$, $J_{11}$ and $J_{12}$, $J_{11}$ and $J_{13}$, $J_{16}$ and $J_{17}$ or $J_{21}$ and $J_{23}$ are optionally taken together to form a heterocyclic ring of 5 to 7 members; or where $J_{22}$ and $J_{24}$, when taken together, form a heterocyclic ring of 5 to 7 members or a bicyclic imide comprising 4 to 12 carbons, with or without unsaturation and/or with or without substitution; or when $G_1$=$CH(OJ_1)$ and $G_2$=$C(CH_2OJ_3)$, $J_1$ and $J_3$ optionally are bonds from the oxygen atoms of $G_1$ and $G_2$, respectively, to a carbon atom of an acetal-, ketal- or orthoester group $G_7$;

wherein $G_7$=$Q_1(T_1)(T_2)$; or when $G_2$=$C(CH_2OJ_3)$ and $G_3$=$CH(OJ_5)$, $J_3$ and $J_5$ optionally are bonds from the oxygen atoms of $G_2$ and $G_3$, respectively, to a carbon atom of an acetal-, ketal- or orthoester group $G_8$; wherein $G_8$=$Q_1(T_1)(T_2)$; or when $G_3$=$CH(OJ_5)$ and $G_4$=$C(CHOJ_9)$, $J_5$ and $J_9$ optionally are bonds from the oxygen atoms of $G_3$ and $G_4$, respectively, to a carbon atom of an acetal-, ketal- or orthoester group $G_9$;

wherein $G_9$=$Q_1(T_1)(T_2)$; or when $G_4$=$C(CHOJ_9)$ and $G_5$=$CH(OJ_{15})$, $J_9$ and $J_{15}$ optionally are bonds from the oxygen atoms of $G_4$ and $G_5$, respectively, to a carbon atom of an acetal-, ketal- or orthoester group $G_{10}$; wherein $G_{10}$=$Q_1(T_1)(T_2)$; or when $G_5$=$C(CHOJ_{15})$ and $G_6$=$CHCH_2(OJ_{19})$, $J_{15}$ and $J_{19}$ optionally are bonds from the oxygen atoms of $G_5$ and $G_6$, respectively, to a carbon atom of an acetal-, ketal- or orthoester group $G_{11}$;

wherein $G_{11}$=$Q_1(T_1)(T_2)$; or when $G_1$=$CH(OJ_1)$ and $G_6$=$CH(CH_2OJ_{19})$ or $CH(OJ_{19})$, $J_1$ and $J_{19}$ are optionally bonds from the oxygen atoms of $G_1$ and $G_6$, respectively, to a carbon atom of an acetal-, ketal- or orthoester group $G_{12}$;

wherein $G_{12}$=$Q_1(T1)(T_2)$;

wherein $Q_1$ is a carbon atom; and $T_1$=H, $CF_3$, alkyl, cycloalkyl, arylalkyl or aryl;

$T_2$=H, $OT_3$, $CF_3$, alkyl, cycloalkyl, arylalkyl, aryl or heterocycle of 5 to 7 members;

$T_3$=alkyl, cycloalkyl, arylalkyl or aryl; or $T_1$ and $T_2$, when taken together, form a carbocyclic ring of 5 or 6 members, with or without unsaturation and with or without substitution; or $Q_1(T_1)(T_2)$ is taken together to form a carbonyl, such that a cyclic carbonate is formed.

The furanosyl- and pyranosyl moieties independently can be in the D-configuration or in the L-configuration, with the D-configuration being preferred in each case. When E is oxygen, the furanose is preferably in the P-configuration and most preferably is in the β-D-configuration.

In general, alkyl groups include 1 to 8 carbons, either straight chained or branched, with or without unsaturation and with or without heteroatoms;

cycloalkyl groups include from 3 to 8 carbons, with or without unsaturation, and with or without heteroatoms;

arylalkyl groups include from 1 to 5 carbons in the alkyl portion, and with monocyclic or polycyclic moieties from 4 to 8 carbons per ring, with or without heteroatoms in the aryl portion;

aryl groups include cyclic moieties from 4 to 10 carbons, with or without heteroatoms; and these groups optionally bear substituents.

Substituents on the foregoing groups inculde, but are not limited to, hydroxy, nitro, methoxy, fluoro, chloro, bromo, iodo, methyl, ethyl, propyl, butyl, benzyl, thioalkyl, alkoxy, carboxyl, cyano, amino, substituted amino, trifluoromethyl, phenyl, cyclopropyl, cyclopentyl, and cyclohexyl. Preferred heteroatoms are oxygen, nitrogen, and sulfur.

Preferred embodiments of the present method are:

where $G_1$=O, and the glycosidic linkage G2-O is the alpha anomer; or where $G_1$=O, and the glycosidic linkage G2-O is the alpha anomer and the pyranose is a D-enantiomer; or where Z=$NZ_3$, $CH_2$, CHF, $CF_2$, $CCl_2$, or CHCl; or where $Z_1$ and/or $Z_2$=S; or where Z=$Z_1$=$Z_2$=O; or where $G_1$=$CH(OJ_1)$, $G_3$=$CH(OJ_5)$, $G_4$=$CH(OJ_9)$, $G_5$=$CH(OJ_{15})$, and $G_6$=$CH(OJ_{19})$ (i.e. $G_1$–$G_6$ represent an inositol or derivative); and the stereoismer is that of myo-inositol with $G_2$ as the 2-position.

A more preferred embodiment includes all of the above, and $X_1$=O and $R_4$=H, $X_2$=$X_3$=H, $E_1$=$E_2$=H and $Y_1$=$Y_2$=O and $M_1$=$M_2$=H (i.e. the nucleoside is uridine).

Preferred compounds of Formula I useful for the present method are:

$X_1$=O, NR, S; or $X_1$ represents a bond from the pyrimidine ring to $R_4$;

$X_2$=H, F, Cl, Br, I, $CF_3$, alkyl, cycloalkyl, arylalkyl, aryl, arylalkenyl, arylalkynyl, $C(O)OR_{17}$, $C(O)NR_{16}R_{18}$ or heterocycle of 5 to 7 members;

$X_3$=H, CN, C(O)OR$_{33}$,;

R=H, alkyl, cycloalkyl, arylalkyl, aryl;

$Y_1$=O; or $Y_1$ represents a bond from the point of ring attachment to $M_1$;

$Y_2$=O; or $Y_2$ represents a bond from the point of ring attachment to $M_2$;

$M_3$=alkyl, cycloalkyl, arylalkyl, or aryl;

$M_4$=alkyl, cycloalkyl, arylalkyl or aryl;

$A_1$=H, alkyl, cycloalkyl, arylalkyl or aryl;

$A_2$=H, alkyl, cycloalkyl, arylalkyl, aryl or heterocycle of 5 to 7 members; or where $A_1$ and $A_2$, when taken together, form a carbocyclic ring of 5 or 6 members, with or without unsaturation, and with or without substitution; or $M_1Q(A_1)(A_2)M_2$ is taken together to form a carbonyl bonded to $Y_1$ and $Y_2$, such that a cyclic carbonate is formed;

Z=O, CH$_2$, CF$_2$, or CCl$_2$;

$G_2$=CH, C(CH$_2$OJ$_3$), or C(CO$_2$J$_4$);

$J_3$=alkyl or C(O)J$_2$;

$J_4$=alkyl;

$J_5$=H, alkyl or C(O)J$_6$;

$J_7$=H, or alkyl;

$J_9$=H, alkyl or C(O)J$_{10}$;

$J_{13}$=H, alkyl, or C(O)J$_{14}$;

$J_{15}$=H, alkyl, or C(O)J$_{16}$;

$J_{17}$=H, alkyl, or C(O)J$_{18}$;

$J_{21}$=H, alkyl, C(O)J$_{22}$ or heterocyclic ring of 5 to 7 members;

$T_1$=H, alkyl, or arylalkyl;

$T_2$=H, alkyl, arylalkyl, or heterocycle of 5 to 7 members; or $T_1$ and $T_2$, when taken together, form a carbocyclic ring of 5 or 6 members, with or without unsaturation and with or without substitution; or $Q_1(T_1)(T_2)$ is taken together to form a carbonyl, such that a cyclic carbonate is formed.

Other preferred compounds of Formula I useful for the present method are:

$X_1$=O, NR, S;

$X_2$=H, F, Cl, Br, I, CF$_3$, alkyl, arylalkyl, aryl, arylalkenyl, arylalkynyl, or heterocycle of 5 to 7 members;

$X_3$=H;

R=H, alkyl, cycloalkyl, arylalkyl, aryl;

$R_4$=H, alkyl, cycloalkyl, arylalkyl, aryl, or C(O)R$_5$;

$R_5$ is H, alkyl, cycloalkyl, arylalkyl, aryl or heterocyclic ring of 5 to 7 members;

$E_1$ and $E_2$ are H;

$Y_1$=O;

$Y_2$=O;

$M_1$ and $M_2$ are independently H, alkyl, cycloalkyl, arylalkyl, aryl, C(O)M$_3$;

$M_3$=alkyl, cycloalkyl, arylalkyl, or aryl;

$A_1$=H, alkyl, cycloalkyl, arylalkyl or aryl;

$A_2$=H, alkyl, cycloalkyl, arylalkyl, or aryl;

Z=O, CH$_2$, CF$_2$, or CCl$_2$;

$G_1$=O or S;

$G_2$=CH;

$G_3$=CH$_2$, CH(OJ$_5$) or CH(NJ$_6$J$_7$);

$G_4$=CH$_2$, CH(OJ$_9$), or CH(NJ$_{11}$J$_{13}$);

$G_5$=CH$_2$, CH(OJ$_{15}$), or CH(NJ$_{16}$J$_{17}$);

$G_6$=CH$_2$, CH(CH$_3$), CH(OJ$_{19}$), CH(CH$_2$OJ$_{19}$), CH(CH$_2$(NJ$_{21}$J$_{23}$)), or CH(CO$_2$J$_{21}$), with the provision that when $G_1$=O or S, then $G_6$ does not equal CH(OH); and the number of hydrogen atoms bonded to the $G_1$–$G_6$ ring atoms is limited to a maximum of 8;

also with the provision that the number of nitrogen atoms bonded to the $G_1$–$G_6$ ring atoms in Formula I is limited to a maximum of 2;

$J_6$, $J_{11}$, and $J_{16}$ are independently H, alkyl, arylalkyl, or aryl;

$J_5$=H, alkyl or C(O)J$_6$;

$J_7$=H, or alkyl;

$J_9$=H, alkyl or C(O)J$_{10}$;

$J_{13}$=H, alkyl, or C(O)J$_{14}$;

$J_{15}$=H, alkyl, or C(O)J$_{16}$;

$J_{17}$=H, alkyl, or C(O)J$_{18}$;

$J_{19}$=H, alkyl, or C(O)J$_{20}$;

$J_{21}$=H, alkyl, or C(O)J$_{22}$; and $J_{23}$=H, alkyl, or C(O)J$_{24}$.

Description of Novel Composition

The present invention is also directed to the following novel compounds and pharmaceutical compositions comprising such compounds in a pharmaceutical acceptable carrier.

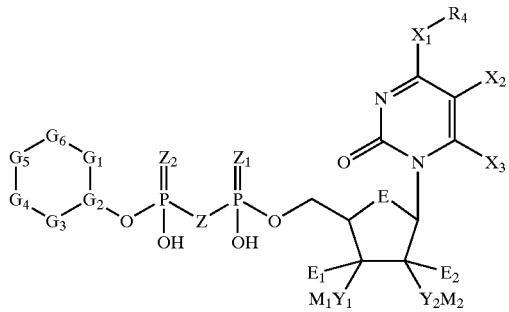

Formula IA wherein:

$R_4$=alkyl, cycloalkyl, arylalkyl, aryl, heterocyclic ring of 5 to 7 members, C(O)R$_5$, C(O)OR$_6$ or C(O)NR$_5$R$_7$;

$X_1$, $X_2$, $X_3$, R, $R_1$–$R_3$, $R_5$–$R_{35}$, E, $E_1$, $E_2$, $Y_1$, $Y_2$, $M_1$–$M_5$, $A_1$–$A_3$, Z, $Z_1$–$Z_3$, $G_1$–$G_6$, $J_1$–$J_{24}$, $G_1$–$G_{12}$, $T_1$–$T_3$ are the same as those described in Formula I.

Formula IB

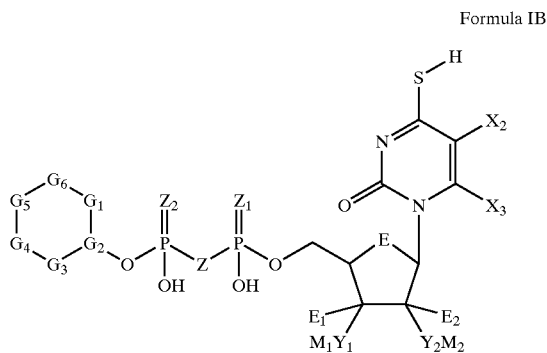

wherein:
$X_2$, $X_3$, R, $R_1$–$R_3$, $R_5$–$R_{35}$, E, $E_1$, $E_2$, $Y_1$, $Y_2$, $M_1$–$M_5$, $A_1$–$A_3$, Z, $Z_1$–$Z_3$, $G_1$–$G_6$, $J_1$–$J_{24}$, $G_1$–$G_{12}$, $T_1$–$T_3$ are the same as those described in Formula I;
provided that when $E=Y_1=Y_2=Z=Z_1=Z_2=G_1=O$, $E_1=E_2H$, $G_2=CH$, $G_3=CH(OJ_5)$, $G_4=CH(OJ_9)$, $G_5=CH(OJ_{15})$ and $G_6=CH(CH_2OJ_{19})$, then at least one of $X_2$, $X_3$, $M_1$, $M_2$, $J_5$, $J_9$, $J_{15}$, or $J_{19}$ is not equal to H.

Formula IC

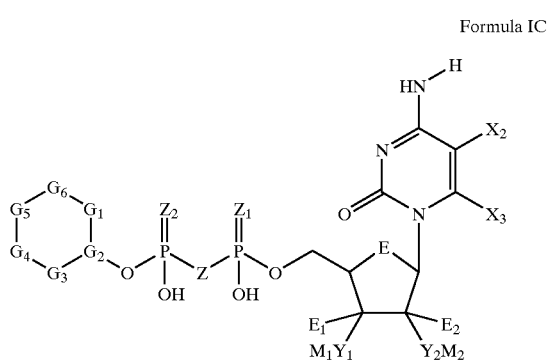

wherein
$X_2$, $X_3$, R, $R_1$–$R_3$, $R_5$–$R_{35}$, E, $E_1$, $E_2$, $Y_1$, $Y_2$, $M_1$–$M_5$, $A_1$–$A_3$, Z, $Z_1$–$Z_3$, $G_1$–$G_6$, $J_1$–$J_{24}$, $G_1$–$G_{12}$, $T_1$–$T_3$ are the same as those described in Formula I;
provided that when $E=Y_1=Y_2=Z=Z_1=Z_2=O$, $G_1=O$ or CH(OH), $E_1=E_2=H$, $G_2=CH$, $G_3=CH(OJ_5)$, $G_4=CH(OJ_9)$, $G_5=CH(OJ_{15})$ and $G_6=CH(CH_2OJ_{19})$, then at leat one of $X_2$, $X_3$, $M_1$, $M_2$, $J_5$, $J_9$, $J_{15}$, or $J_{19}$ is not equal to H;
further provided that when $X_2=H$ or $CH_2OH$, $E=Y_{1=Z=} z_1=Z_2=G_1=O$, $Y_2$=bond to $M_2$ from ring, $E_1=E_2=M_2=H$, $G_2=CH$, $G_3=CH(OJ_5)$ and $G_4=CH(OJ_9)$, $G_5=CH(OJ_{15})$, $G_6=CH(CH_2OJ_{19})$, then at least one of $X_3$, $M_1$, $J_5$, $J_9$, $J_{15}$, or $J_{19}$ is not equal to H;
further provided that when $E=Y_1=Y_2=Z=Z_1=Z_2=G_1=O$, $E_1=E_2=H$, $G_2=CH$, $G_3=CH(OJ_5)$, $G_4=CH_2$, $G_5=CH(OJ_{15})$, $G_6=CH(CH_3)$, then at least one of $X_2$, $X_3$, $M_1$, $M_2$, $J_5$, or $J_{15}$ is not equal to H;
further provided that when $E=Y_1=Y_2=Z=Z_1=Z_2=G_1=O$, $E_1=E_2=H$, $G_2=CH$, $G_3=CH_2$ or $CH(NH_2)$, $G_4=CH(OJ_9)$, $G_5=CH(OJ_{15})$, $G_6=CH(CH_3)$, then at least one of $X_2$, $X_3$, $M_1$, $M_2$, $J_9$, or $J_{15}$ is not equal to H;
further provided that when $E=Y_1=Y_2=Z=Z_1=Z_2=G_1=O$, $E_1=E_2=H$, $G_2=CH$, $G_3=CH(NH_2)$, $G_4=CH(OJ_9)$, $G_5=CH(OJ_{15})$, $G_6=CH(CH_2(NH_2))$, then at least one of $X_2$, $X_3$, $M_1$, $M_2$, $J_9$, or $J_{15}$ is not equal to H;
further provided that when $E=Y_1=Y_2=Z=Z_1=Z_2=G_1=O$, $E_1=E_2=H$, $G_2=CH$, $G_3=CH(OH)$, $G_4=CH_2$, $G_6=CH(CH_3)$, then $G_5$ is not equal to CHF;
further provided that when $E=Y_1=Y_2=Z=Z_1=Z_2=G_1=O$, $E_1=E_2=X_2=X_3=M_1=M_2=H$, $G_2=CH$, $G_3CH(OH)$, $G_4=CH(OH)$, $G_5=CH(OH)$, then $G_6$ is not $CH(CH_3)$ or $CH(CHF_2)$;
further provided that when $E=Y_1=Y_2=Z=Z_1=Z_2=G_1=O$, $E_1=E_2=H$, $G_2=CH$, $G_3=CH(OH)$, $G_5=CH(OH)$, $G_6=CH(CH_2OH)$ then $G_4$ is not CHF.

Formula ID

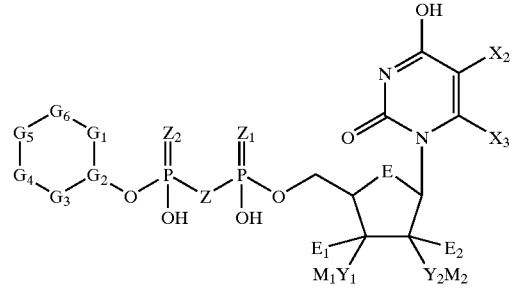

wherein:
$X_3=CN$, $OR_{19}$, $SR_{19}$, $NR_{23}R_{28}$, $CF_3$, alkyl, cycloalkyl, $C(O)R_{32}$, $C(O)OR_{33}$, $C(O)NR_{34}R_{35}$, arylalkyl, aryl, arylalkenyl, arylalkynyl, or a heterocycle of 5 to 7 members;
$X_2$, $X_3$, E, $E_1$, $E_2$, $Y_1$, $Y_2$, $M_1$, $M_2$, Z, $Z_1$, $Z_2$, and $G_1$–$G_6$ are the same as those described in Formula I.

Formula IE

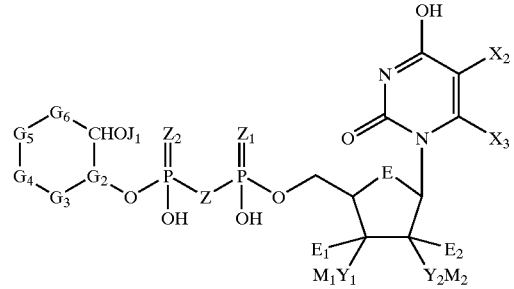

wherein:
$X_2$, $X_3$, $E_1$, $E_2$, $Y_1$, $Y_2$, $M_1$, $M_2$, Z, $Z_1$, $Z_2$, $G_2$–$G_6$ and $J_1$ are the same as those described in Formula I.

Formula IF

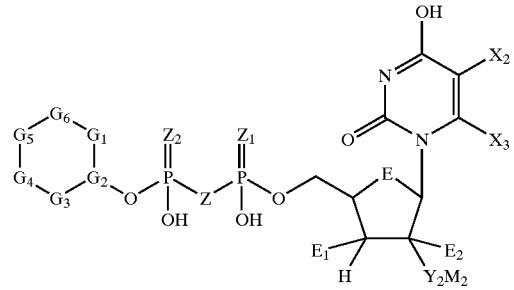

wherein:
$X_2$, $X_3$, $E_1$, $E_2$, $Y_2$, $M_2$, Z, $Z_1$, $Z_2$, $G_2$–$G_6$ are the same as those described in Formula I;

Provided that when $X_2=CH_3$, $X_3=E_1=E_2=M_2=H$, $E=Y_2=Z=Z_1=Z_2=G_1=O$, $G_2=CH$, $G_3=G_4=G_5=CH(OH)$, then $G_6$ is not $CH(CH_3)$ or $CH(CH_2OH)$.

Formula IG

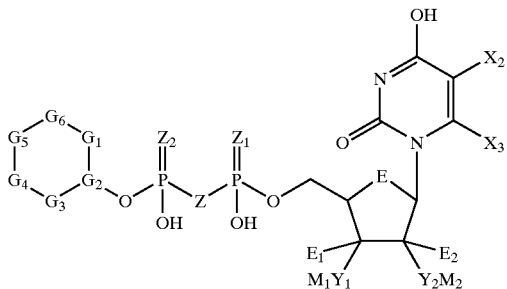

wherein:
- $X_2$ is aryl, arylalkyl, arylalkenyl, arylalkynyl, $C_2$–$C_8$ alkyl, $C_2$–$C_8$ alkenyl, alkynyl, cycloalkyl, or $C_3$–$C_8$ branched alkyl, and none of the alkyl groups in $X_2$ are substituted with an amine or an amide on the chain, or contain a nitrogen hetero atom;
- $X_3$, $E_1$, $E_2$, $M_1$, $M_2$, $Y_1$, $Y_2$, $Z$, $Z_1$, $Z_2$, $G_1$–$G_6$ are the same as those described in Formula I.

Formula IH wherein:
- $X_2$, $X_3$, E, $E_1$, $E_2$, $M_1$, $M_2$, $Y_1$, $Y_2$, $Z$, $Z_1$, $Z_2$, $G_2$–$G_5$ and $J_{21}$ are the same as those described in Formula I;
- provided that when $X_2=X_3=E_1=E_2=M_1=M_2=H$, $E=Y_1=Y_2=Z=Z_1=Z_2=O$, $G_2=CH$, $G_3=G_4=G_5=CH(OH)$, then $J_{21}$ is not H or $CH_3$.

Formula II

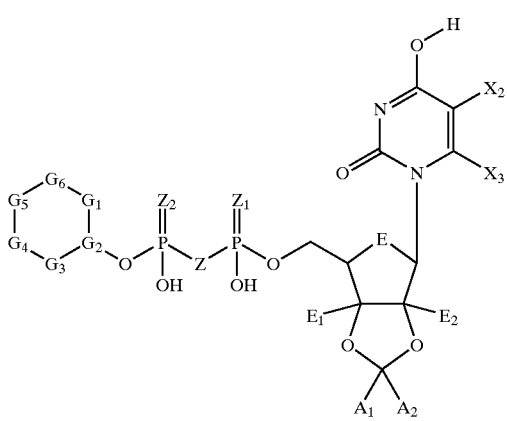

wherein:
- $X_2$, $X_3$, E, $E_1$, $E_2$, $A_1$, $A_2$, $Z$, $Z_1$, $Z_2$ and $G_2$–$G_6$ are the same as those described in Formula I;

provided that when $X_2=X_3E_1=E_2H$, and $E=Z_1=Z_2$ $G_1=O$, and $A_1=A_2=CH_3$, then Z is not equal to $CH_2$ or $CF_2$;

further provided that when $X_2=X_3=E_1=E_2=H$, and $E=Z=Z_1=Z_2=G_1=O$, and $A_1$ and $A_2$ are taken together to form an unsaturated 6-membered ring, then $G_6$ is not $CH(CH_2OH)$.

The present invention also encompasses non-toxic pharmaceutically acceptable salts of the above phosphate derivatives, such as, but not limited to, alkali metal salts such as lithium, sodium or potassium salts, or alkaline earth metal salts such as magnesium or calcium salts; or ammonium or mono-, di-, tri- or tetraalkyl ammonium salts, such as $NH_4^+$, $NLH_3^+$, $NL_2H_2^+$, $NL_3H^+$, or $NL_4^+$(wherein L is $C_{1-4}$ alkyl) salts. Pharmaceutically acceptable salts are salts that retain the desired biological activity of the parent compound and do not impart undesired toxicological effects. Preferred counterions are monovalent ions such as sodium, lithium or potassium.

The present invention also encompasses mixtures of the above materials.

Methods of Preparing the Compounds

The compounds of the present invention can be conveniently synthesized by those skilled in the art using well-known chemical procedures. Nucleoside 5'-pyrophosphate pyranose esters can be obtained from commercial sources or synthesized from the appropriate nucleoside and pyranose using a variety of phosphorylation and coupling reactions found in the chemical literature. Many different nucleosides, nucleotides, pyranose derivatives and inositols are commercially available and can be used as starting materials for these procedures.

Nucleoside 5'-pyrophosphate pyranose esters are prepared by activation of a nucleoside monophosphate with a coupling agent such as, but not limited to, dicyclohexylcarbodiimide or 1,1'-carbonyldiimidazole, followed by condensation with a pyranose 1-phosphate. Alternatively, a 1-bromopyranose is coupled with the silver salt of a nucleoside 5'-pyrophosphate. Another alternative, which is useful in some cases, is the use of an enzyme such as uridine 5'-diphosphoglucose pyrophosphatase and suitable pyranylphosphate and nucleotide triphosphate precursors (Simon, et al., *J. Org. Chem.*, 55: 1834–1841 (1990)).

The compounds of the present invention are prepared by derivatization or substitution at the level of the nucleoside, nucleotide, pyranose or inositol unit, followed by phosphorylation and condensation as previously described; the reactions can alternatively be carried out directly on the pre-formed nucleotide 5'-pyrophosphate pyranose analogue.

In Formula I, the substituents at $Y_1M_1$, $Y_2M_2$, $G_2$, $G_3$, $G_4$, and $G_5$ generally are, but are not limited to, alcohols, ethers, esters, amides, carbamates, carbonates, or acetals. The substituents can be introduced as follows:

Ethers are prepared by reacting a hydroxyl group of the furanose in a nucleoside or a hydroxyl group of a pyranose with an alkylating agent in the presence of a suitable base in an appropriate solvent.

Esters can be readily prepared by reacting a hydroxyl group of the furanose in a nucleoside or nucleotide or a hydroxyl group of a pyranose with an activated form of an appropriate organic acid, such as an acid halide or acid anhydride in the presence of an organic or inorganic base. Alternately, a suitable coupling reagent such as dicyclohexylcarbodiimide, or 1,1'-carbonyldiimidazole is used to activate the organic acid to achieve similar results.

Amides are readily prepared by reacting an amino group of a nucleoside or nucleotide or an amino group of an aminopyranose analogue with an activated form of an appropriate organic acid, such as an acid halide or acid anhydride in the presence of an organic or inorganic base. Alternately, a suitable coupling reagent such as dicyclohexylcarbodiimide, or 1,1'-carbonyldiimidazole is used to activate the organic acid to achieve similar results.

Carbamates are prepared by reaction of a hydroxyl group of the furanose in a nucleoside or nucleotide or a hydroxyl group of a pyranose with any of a number of commercially available isocyanates in an inert solvent. Alternately, when a desired isocyanate is not obtainable from commercial sources, it can be prepared from the corresponding amine by the use of phosgene or a chemical equivalent.

Carbonates are synthesized by reacting the hydroxyl group of a furanose in a nucleoside or nucleotide or a hydroxyl group of a pyranose with an appropriate haloformate in the presence of an organic or inorganic base.

Nucleosides are converted into nucleotide monophosphates using phosphorous oxychloride in trimethyl phosphate. Hydrolysis and workup, followed by chromatographic purification gives the corresponding monophosphate derivatives. Monophosphates can be further modified to give diphosphates using literature procedures.

Nucleosides are alternatively converted into nucleotide diphosphates using pyrophosphoryl chloride in trimethyl phosphate. Hydrolysis and workup, followed by chromatographic purification gives the corresponding diphosphate derivatives. Alternatively, a pyrophosphate, imidodiphosphate or methylene-bisphosphonate unit is coupled to a nucleoside by reaction of a tributylammonium salt of one of the above acids with the appropriate nucleoside 5'-tosylate, -mesylate, -iodide or -bromide in an appropriate solvent such as dimethylsulfoxide. Workup, followed by chromatographic purification gives the corresponding diphosphate, imidodiphosphate, or methylene-bisphosphonate derivative.

Pyranose derivatives are converted into pyranose 1-phosphates via the corresponding pyranose 1-bromides or other activated pyranosides by reaction with a promoter such as a silver phosphate salt, followed by hydrolysis, workup and chromatography.

In Formula I, the substituents at $Y_1M_1$ and $Y_2M_2$ are optionally taken together to form acetals, ketals or orthoesters. Similarly, vicinal-, or homovicinal hydroxyl groups, when present on the $G_1$–$G_6$ ring in Formula I, are optionally taken together to form acetals, ketals or orthoesters. Acetals and ketals are prepared by reaction of the vicinal hydroxyl groups on a furanose, pyranose, inositol, appropriate nucleoside or appropriate nucleotide derivative with an aldehyde or ketone, or their chemical equivalents, respectively, in the presence of an acid catalyst.

Similarly, cyclical orthoesters are prepared by reaction of vicinal hydroxyl groups of a faranose, pyranose, inositol, appropriate nucleoside or appropriate nucleotide derivative with an acylic orthoester in the presence of an acid.

When a nucleoside or nucleotide to be derivatized is a pyrimidine that contains a 4-amino functionality, it is converted to the respective urea by treatment with isocyanates as was previously described for carbamates of the 2'- or 3'-hydroxyls of the furanose ring. It has been found that reactions of the amino group with isocyanates can be carried out in the presence of the hydroxyl groups of the furanose, by appropriate manipulation of the stoichiometry of the reaction.

Many of the derivatization reactions described are carried out on preformed nucleoside 5'-pyrophosphate pyranose esters, which result in multiple products. Relative product ratios depend upon reaction stoichiometry and on whether multiple reactive groups are present. When multiple products are obtained, these are separated by the use of preparative reverse-phase high performance liquid chromatography (HPLC). Particularly advantageous is the use of C18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Furthermore, the use of ammonium acetate buffer solutions in conjunction with methanol allows the chromatographed products to be isolated following evaporation and lyophilization of the volatile salt.

While separation of multiple products can be done by HPLC, another strategy to increase the yield of desired product from a reaction sequence is to first introduce protecting groups into nucleoside-, nucleotide- and/or pyranose starting materials. This strategy produces materials having a single reactive functionality available for reaction with a subsequent reagent. Protecting groups are introduced on preformed nucleoside 5'-pyrophosphate pyranose esters, or alternately, are carried out on nucleosides, nucleoside monophosphates, pyranoses and/or pyranose phosphates. These materials are purified by chromatography or other means. Further functionalization, followed by deprotection leads to a selectively-functionalized product. This new material is used in further condensation reactions, or can be the end product desired in the sequence.

Those having skill in the art will recognize that the starting materials and additional steps employed to produce compounds encompassed by the present invention can be varied. In some cases, protection of certain reactive functionalities is preferred to achieve some of the above transformations. In general, the need for such protecting group synthesis as well as the conditions necessary to attach and remove such groups will be apparent to those skilled in the art of organic synthesis.

Methods of Administration

The active compounds disclosed herein are administered to the eyes of a patient by any suitable means, but preferably administered by administering a liquid or gel suspension of the active compound in the form of drops, spray or gel. Alternatively, the active compounds are applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses, which are placed on the eye. Another embodiment of the present invention involves the active compound contained within a swab or sponge, which is applied to the ocular surface. Another embodiment of the present invention involves the active compound contained within a liquid spray, which is applied to the ocular surface. Another embodiment of the present invention involves an injection of the active compound directly into the ocular tissues, such as subconjunctival, subscleral, or intravitrial injection, or onto the eye surface.

The quantity of the active compound included in the topical solution is an amount sufficient to achieve dissolved concentrations of the active compound on the ocular surface of the subject of from about $10^{-7}$ to about $10^{-1}$ moles/liter, and preferably from about $10^{-6}$ to about $10^{-2}$ moles/liter, and more preferably from about $10^{-4}$ to about $10^{-2}$ moles/liter in order to decrease intraocular pressure.

The topical solution containing the active compound can also contain a physiologically compatible vehicle, as those skilled in the ophthalmic art can select using conventional criteria. The vehicles can be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound is absorbed into the bloodstream via the lungs and subsequently contact the ocular tissues in a pharmaceutically effective amount. The respirable particles are a liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles which the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing active compounds are in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use are be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, or liquid suspension form of a therapeutically effective amount of the active compound.

The method of the present invention is optionally used with other therapeutic and adjuvant agents commonly used to reduce intraocular pressure, thus enhances the effects of therapeutic agents and adjunctive agents used to treat and manage the different types of glaucoma. Therapeutic agents used to treat narrow angle or acute congestive glaucoma include, for example, physostigmine salicylate and pilocarpine nitrate. Adjunctive therapy used in the management of narrow angle glaucoma includes, for example, the intravenous administration of a carbonic anhydrase inhibitor such as acetozolamide to reduce the secretion of aqueous humor, or of an osmotic agent such as mannitol or glycerin to induce intraocular dehydration. Therapeutic agents used to manage wide angle or chronic simple glaucoma and secondary glaucoma include, for example, prostaglandin analogs, such as Xalatan® and Lumigan®, beta-adrenergic antagonists such as timolol maleate, alpha-adrenergic agonists, such as brimonidine and apraclonidine, cholinergic agents, such as pilocarpine, and carbonic anhydrase inhibitors, such as Dorzolamide®.

High doses may be required for some therapeutic agents to achieve levels to effectuate the target response; such high doses often lead to a greater frequency of dose-related adverse effects. Thus, combined use of the compounds of the present invention with agents commonly used to treat glaucoma allows the use of relatively lower doses of such agents resulting in a lower frequency of adverse side effects associated with long-term administration of such therapeutic agents. Thus, another advantage of the compounds in this invention is to reduce adverse side effects of drugs used to treat glaucoma, such as the development of cataracts with long-acting anticholinesterase agents including demecarium, echothiophate, and isoflurophate.

The invention is illustrated further by the following examples that are not to be construed as limiting the invention in scope to the specific procedures described in it.

EXAMPLES

Example 1

Effects of Uridine 5'-Diphosphate-α-D-Glucose on Intraocular Pressure

The action of uridine 5'-diphosphate-α-D-glucose (Compound INS25285) on intraocular pressure (IOP) was assessed in New Zealand white rabbits.

Intraocular pressure measurements: IOP was measured using a TONOPEN contact tonometer supplied by MENTOR (USA). Ten microliters of the agents were applied topically and unilaterally to the cornea, whereas the contralateral eye received the same volume of saline solution. The corneas were anesthetized to avoid any discomfort associated with the use of the tonometer. Two measurements were made before application of the agents.

Pharmacological studies: Compound was prepared at a concentration of 1.0 mM in 0.9% saline and intraocular pressure was measured at −0.5, 0, 0.5 hours, and hourly up to 9 hours after the application.

Effect of Compound INS25285 on rabbit IOP: INS25285 produced a time-dependent reduction in IOP, which was maximal from 0.5 to 5 hours with a reduction of 26% (n=4) (FIG. 1). This lowering of intraocular pressure in rabbits by compound INS25285 demonstrates the utility of uridine 5'-diphosphate-α-D-glucose for treating ocular hypertension and glaucoma.

It should be apparent that given the guidance, illustrations and examples provided herein, various alternate embodiments, modifications or manipulations of the present invention would be suggested to a skilled artisan and these are included within the spirit and purview of this application and scope of the expanded claims.

What is claimed:

1. A method of reducing intraocular pressure comprising administering to a subject a pharmaceutical composition comprising an effective amount of a compound of Formula I, its diastereomers, enantiomers, tautomers, or pharmaceutically acceptable salts thereof:

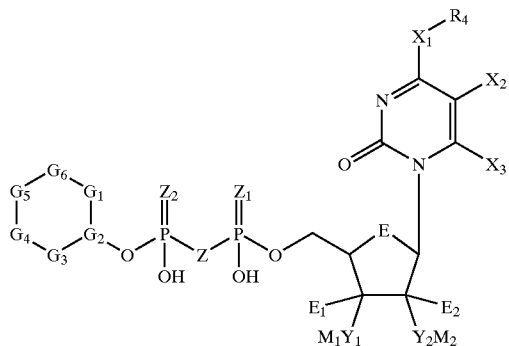

wherein:
$X_1$=O or S;
$X_2$=H, F, Cl, Br, I, CN or alkyl;
$X_3$=H;
$R_4$=H;
E=O;
$E_1$ and $E_2$ independently are H or F;
$Y_1M_1$ and $Y_2M_2$ are independently OH, F, or H;
Z=O, NH, $CH_2$, CHF, $CF_2$, $CCl_2$, or CHCl;
$Z_1$ and $Z_2$ are independently O or S;
$G_1$=O or S;
$G_2$=CH;
$G_3$=$CH_2$, CHF, $CF_2$, CH(OH) or CH($NHJ_7$);
$G_4$=$CH_2$, CHF, $CF_2$, CH(OH) or CH($NHJ_{13}$);
$G_5$=$CH_2$, CHF, $CF_2$, CH(OH) or CH($NHJ_{17}$);
$G_6$=$CH_2$, CH($CH_2OH$);
the number of hydrogen atoms bonded to the $G_1$–$G_6$ ring atoms is limited to a maximum of 8;
also with the provision that the number of nitrogen atoms bonded to the $G_1$–$G_6$ ring atoms in Formula I is limited to a maximum of 2;

$J_7$, $J_{13}$, and $J_{17}$ are independently H, C(O)H, or C(O)alkyl.

2. The method according to claim 1, wherein:

Z=O, $CH_2$, $CF_2$, or $CCl_2$.

3. The method according to claim 2, wherein:

$G_3$=$CH_2$, CH(OH), or CH($NHJ_7$);

$G_4$=$CH_2$, CH(OH), or CH($NHJ_{13}$);

$G_5$=$CH_2$, CH(OH), or CH($NHJ_{17}$).

4. The method according to claim 1, wherein said method further comprises the step of measuring the intraocular pressure of said subject before administering the composition.

5. The method according to claim 1, further comprising the step of measuring the intraocular pressure of said subject after administering the composition.

6. The method according to claim 1, wherein administering said pharmaceutical composition to said subject is to treat ocular hypertension.

7. The method according to claim 6, wherein administering said pharmaceutical composition to said subject is to treat glaucoma.

8. The method according claim 1, wherein said pharmaceutical composition is co-administered to said subject with other therapeutic agent or adjuvant therapy commonly used to reduce intraocular pressure.

9. The method according to claim 1, wherein said pharmaceutical composition is administered topically to said subject.

10. The method according to claim 1, wherein said pharmaceutical composition is administered via subconjunctival, subscleral, or intravitreal injection to said subject.

11. The method according to claim 1, wherein said compound is uridine 5'-diphospho-α-glucose.

* * * * *